United States Patent
Zofchak et al.

(10) Patent No.: US 6,365,629 B1
(45) Date of Patent: Apr. 2, 2002

(54) FATTY ACID ESTERS OF AROMATIC ALCOHOLS AND THEIR USE IN COSMETIC FORMULATIONS

(75) Inventors: Albert Zofchak, Matawan; Madeline Kenney, Caldwell; Jebidiah Jordan, Highland Park; Rustico Payumo, Passaic, all of NJ (US)

(73) Assignee: Alto, Inc., Sayreville, NJ (US)

( * ) Notice: Subject to any disclaimer, the term of this patent is extended or adjusted under 35 U.S.C. 154(b) by 0 days.

(21) Appl. No.: 09/307,926

(22) Filed: May 10, 1999

(51) Int. Cl.[7] .............................................. A01N 37/02
(52) U.S. Cl. ...................... 514/552; 515/549; 515/873; 554/229; 424/59; 424/60; 424/64; 424/73
(58) Field of Search .................... 554/229; 514/887, 514/546, 557, 549, 552, 873; 424/63, 64, 401, 59, 60, 73

(56) References Cited

U.S. PATENT DOCUMENTS

| | | |
|---|---|---|
| 5,833,964 A | 11/1998 | Linn et al. |
| 5,932,197 A * | 8/1999 | Arnaud ........................ 424/64 |
| 5,972,319 A * | 10/1999 | Linn et al. .................... 424/65 |

FOREIGN PATENT DOCUMENTS

WO    WO 97/34577    9/1997

OTHER PUBLICATIONS

Linn et al, US citation for U.S. Patent No. 5,972,319 registry file AN 1998:682090.*

Ishigami et al, Preparation of Carboxyalkyl Sophorosides as Biodegradable Surfactants, AN 1995:708628, (see abstract and citation), 1995.*

Linn et al, Low Residue antiperspirant stick composition, AN 1997:640521 CAPLUS (abstract and citation).*

* cited by examiner

Primary Examiner—Deborah D. Carr
(74) Attorney, Agent, or Firm—H. Coleman; R. N. Sudol; W. J. Sapone

(57) ABSTRACT

The present invention relates to compounds according to the structure:

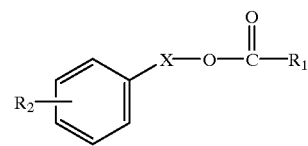

Wherein $R_1$ is a $C_{11}$ to $C_{21}$ saturated or unsaturated, linear or branched hydrocarbon or a saturated or unsaturated hydrocarbon containing a pendant hydroxyl group, preferably on a carbon atom in a position alpha or beta to the keto group of the ester moiety;

X is $CH_2$, $OCH_2CH_2$ or $HC=CHCH_2$; and $R_2$ is H, $OCH_3$, $CH_3$ or $CH_2CH_3$. These compounds exhibit use in personal care products as dry emollients as well as providing additional characteristics including solvency, dispersants, gloss-enhancing agents, solubilizing agents and melting-point depressants, lubricants, viscosity modulating agents and skin protection factor boosters.

24 Claims, No Drawings

FATTY ACID ESTERS OF AROMATIC ALCOHOLS AND THEIR USE IN COSMETIC FORMULATIONS The present invention is directed to fatty acid acid esters of monohydric aromatic alcohols and their use as "dry" emollients and their solvency characteristics for active ultraviolet absorbers and dispersibility and anti-agglomeration properties for inorganic sunblocks with resultant increase in SPF values of cosmetic formulations.

BACKGROUND OF THE INVENTION

Over the years, numerous esters have been commercially prepared from fatty alcohols and fatty acids ranging in chain lengths from $C_1$ to $C_{50}$ and have been successfully used as emollients, solubilizers, clarifying agents, pearlescing agents, dispersants, sunscreens, coupling agents, emulsifying agents, viscosity building agents, opacifying agents, conditioning agents, defoliants, anti-irritants, tackifiers, detackifiers, spreading agents, blooming agents, slip additives, glossifying agents, spreading agents, melting point depressants, etc. Generally speaking, esters have been prepared by direct esterification between an alcohol and an acid using either an acid or basic catalyst; esters have also been prepared by transesterification between two esters or by transesterification under either basic or acid catalysis of oils with various alcohols to produce the resultant ester.

Esters have been derived from purely naturally occurring raw materials such as triglycerides of coconut, sunflower, safflower, soybean, babbasu, rapeseed, canola, mink, tallow, lard oil, apricots, etc. Esters have also been derived and used in the cosmetic, toiletry as well as the personal care area from purely derived synthetic sources such as Isopropanol, Butanol, 2-Ethylhexanol, Isodecanol, Isononyl Alcohol, Tridecanol, Isocetyl Alcohol, Isostearyl Alcohol, Octadecanol, $C_{20}$+Alcohols and may be linear, isomeric or branched in character and have been monohydric. Esters have also been produced and used on a commercial basis in the cosmetic, toiletry and personal care industries based on diols, triols, tetraols and various polyols such as sugars and sorbitols reacted with acids ranging in chain lengths from $C_1$ through $C_{50}$. Similarly, esters have been produced from dimer, trimer, tetra as well as Polycarboxylic Acids with alcohols ranging from $C_1$ to $C_{50}$. Esters have also been prepared from Alkoxylated Alcohols and Alkoxylated Acids to yield emulsifiers with various degrees of water and oil insolubility/solubility commonly referred to as HLB.

Similarly, esters from alfa as well as beta-hydroxyacids have been prepared and used primarily as defoliating agents for the skin and conditioning agents for the hair. Lauryl Lactate, for example has been found to serve as a vehicle for transporting active drugs through the skin.

Esters of Salicylic Acid have been used as sunscreens and also have been used as sunscreen synergists as well as defoliants for the skin. Esters have also been prepared from derivatives of Cinnamyl derivatives, i.e, Octylmethoxy Cinnamate and 2-Ethyl Hexanol ester of p-Dimethylamino Benzoic Acid for use as sunscreen to effectively aborb UV light.

Esters, derived from Benzoic Acid, have been prepared and commercially used in the cosmetic, toiletry and personal care industry. Typical examples here are the well-known $C_{12}$–$C_{15}$ ester of Benzoic Acid as well as the Benzoic Acid ester of Glycereth-7. Esters have also been used in the cosmetic, toiletry and personal care areas as preservatives such as methyl, propyl and butyl esters of p-amino Benzoic Acid and solutions of these esters and Phenoxyethanol and similar solvents.

Esters derived from pentaerithritol are also used in the cosmetic, toiletry and personal care areas. These esters are tetra-functional and are known for their lubricity characteristics inasmuch as they can be defined structurally as simulating "ball-bearings". In essence, they tend to be circular rather than linear as are most esters.

Linear esters tend to exhibit characteristics of "slip and slide". Esters of lactic acid are known for the spreading properties. Esters derived from unsaturated or partially unsaturated isoalcohols or isoacids tend to exhibit liquidity at ambient temperatures making them easy to work with in actual production circumstances.

Esters have been prepared from ethoxylated alcohols and acids, linear or isomeric, and have been found to function as excellent emulsifiers. By varying the degree of ethoxylation of either the alcohol or acid and the ultimate esterification of the terminal hydroxyl group, it is possible to achieve a wide spread of HLB values. Esters prepared from propoxylated alcohols or acids have been found to "yield" emolliency; however, such emollients tend to be quite heavy with "drag".

Esters, therefore, serve many different aspects in the cosmetic, toiletry and personal care areas and find use in numerous applications. Esters produced from Dimer Acids or Dimer Alcohols are primarily known for their anti-irritating characteristics when employed in a formulation. However, they tend to be quite "heavy".

Esters prepared from Adipic Acid, Azaleic Acid, Dodecanedioic Acid, Sebacic Acid and Maleic Acid tend to yield esters with good low temperature characteristics. However, most of these esters are quite "heavy" with the exception of Diisopropyl Adipate because of the use of di-alcoholic groups of isopropanol yields a "light" ester and has found use in deodorants and bath products. Further, being based on rather low cost raw materials, i.e., Adipic Acid and Isopropanol, it is more than reasonably priced for large use commodity products sold in the cosmetic, toiletry and personal care market. In essence, esters can be prepared from mono-, di-, tri-, tetra- or poly-functional acids of alcohols and can serve many useful purposes in the cosmetic, toiletry and personal care areas as defined below:

Emolliency
Emulsification
Conditioning
Defoliation
Blooming Agent
Clarification
Dispersion
Coupling
Solubilization
Freeze Point Depressant
Spreading Agent
Gloss Enhancing
Tackifying
De-tackifying
Slip Additive
Anti-irritant
Solvent for Sunscreens/Other Active Ingredients
Insect Repellents
Vehicles for Inorganic Sunscreens Esters have been used to replace naturally occurring oils and waxes; i.e., Spermacetic wax and sperm oil have been successfully used for years via esters such as Cetyl Myristate, Cetyl Palmitate and mixed cetyl esters, thereby saving the whale. Synthetics such as octyldodecyl erucate have successfuly replaced jojoba oil, which has been known to vacillate in price due to changes in weather.

Of all of the esters elucidated above, none have been derived from aromatic alcohols such as benzyl or phenoxyethanol in the cosmetic, toiletry and personal care areas.

Esters derived from benzyl alcohol, and phenoxyethanol have been used in large volumes in the perfume industry, more specifically, acid derivatives of twelve carbon atoms ($C_{12}$) or less; inasmuch as, such molecules exhibit sufficient vapor pressure to exert sufficient volatility to "evaporate" and exert the effect of a perfume. Listed below is a compendium of various benzyl, phenoxyethyl and anisyl alcohol derivatives that have been and currently are being used as "fragrance intermediates" finding use in a variety of fragrance products and masking agents in numerous industries:

| | |
|---|---|
| Benzyl Acetate | Powerful, but thin, sweet, fresh floral note. Also used in flavors. |
| Benzyl Benzoate | Faint, sweet balsamic odor used widely in fixatives. |
| Benzyl Caproate | Sweet, fruit slightly green odor. Used in immitation pineapple and apricot flavors. |
| Benzyl Laurate | Very faint, fatty odor. Used primarily as a fixative in perfumes. |
| Benzyl Myristate | Diluent for fatty aldehyde in fragrances. |
| Benzyl Pelargonate | Faint, fresh balsamic odor. Used as a fixative. |
| Benzyl Propionate | Fruity, sweet odor. Used in flavor. |
| Benzyl Valerate | Powerful, fruity and somewhat musky. Used in fragrances. |
| Phenoxyethyl Acetate | Sweet floral odor of good tenacity. |
| Phenoxyethyl-iso-Butyrate | Sweet-fruity, rosy-floral, slightly honey-like odor of excellent tenacity. |
| Phenoxyethyl Propionate | Warm, rosy-fruity, slightly earthy. Herbaceous odor of good tenacity. |
| Phenoxyethyl-iso-Valerate | Warm-fruity-floral odor of considerable tenacity. |
| Phenoxypropyl Butyrate | Sweet, milky-fruity-honey-like, tenacious odor. |
| Anisyl Alcohol | Mild-floral, very sweet odor, reminiscent of Lilac and Vanilla with a faint delicate balsamic background. |
| Anisyl Benzoate | Very faint, balsamic-floral odor of great tenacity. |
| Anisyl Butyrate | Mild floral, intensely sweet and warm-slightly fruity, plum-like odor. |
| Anisyl Formate | Sweet herbaceous-green, reminiscent of Vanilla beans (cured) with an exotic-floral background. |
| Anisyl Heptoate | Very faint fruity odor, reminiscent of Peach or Apricot juice. Very tenacious. |
| Anisyl Propionate | Sweet fruity, floral and somewhat Vanilla-like odor. |
| Anisyl Valerate | Very sweet, fruit-Apricot-Nectarine Grenadine-like odor. |

OBJECTS OF THE INVENTION

It is the object of the current invention to provide unique and novel applications of the esters of fatty acids of aromatic alcohols, e.g., benzyl alcohol, phenoxyethyl alcohol and anisyl alcohol and the like to provide "dryness" for use as emollients in the cosmetic industry.

It is a further object of the present invention to provide esters of aromatic alcohols, i.e., benzyl alcohol and phenoxyethanol, as spreading agents for use in the cosmetic, toiletry and personal care industries.

It is still further the object of the present invention to provide esters which exhibit outstanding solubility charac-teristics for pigments used in the preparation of lip products, i.e., lipsticks and lip balms.

It is yet another object of the present invention to provide outstanding solvents or solubilizing agents for active ultra-violet light absorbers for the well known and established sunscreens such as octyl salicylate, octyl methoxycinnamate, p-dimethylamino benzoic acid ester of 2-ethylhexanol and avo benzone.

It is still another object of the present formula to provide outstanding dispersants for inorganic pigments such as zinc oxide and titanium dioxide which are widely used as sunblocks in the cosmetic, toiletry and personal care areas.

It is yet another object of the present invention to provide "dry" emollients which function as solvents and are compatible with widely used silicone fluids that find use in the personal care, toiletry and cosmetic industries.

It is still another object of the present invention to introduce novel compositions which function as melting point depressants for use in the cosmetic, toiletry and personal care industries.

SUMMARY OF THE INVENTION

The present invention relates to Fatty Acid Esters of Aromatic Monohydric Alcohols according to the following structure:

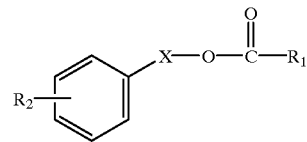

Wherein $R_1$ is a $C_{11}$ to $C_{21}$ saturated or unsaturated, linear or branched hydrocarbon, which is either unsubstituted or substituted with a pendant hydroxyl group, preferably on a carbon atom in a position alpha or beta to the keto group of the ester moiety;

X is $CH_2$, $OCH_2CH_2$ or $HC=CHCH_2$;

and $R_2$ is H, $OCH_3$, $CH_3$ or $CH_2CH_3$.

In preferred compounds according to the present invention, $R_1$ is an unsaturated $C_{17}$ to $C_{21}$ hydrocarbon, most preferably having a pendant hydroxyl group and $R_2$ is preferably H and X is preferably a $CH_2$ (methylene group). $R_2$ may be substituted on the phenyl group (benzene ring) in the ortho, meta or para position.

Compounds of the present invention exhibit primary utility as "dry emollients" which is a characteristic that is deficient in essentially all other commercially available products which are used as emollients in the personal care, cosmetic and toiletry industries. The "dry" emolliency of the present invention is due to the monohydric aromatic alcohol moiety in the final ester product. It has been discovered unexpectedly that the "dryness" of the emollients according to the present invention occurs even where $R_1$ is a long chain hydrocarbon derived from the corresponding monocarboxy-lic acid, tends to impart slip and oiliness. Quite unexpectedly, the degree of dryness of the present compounds is influenced by the degree of unsaturation of the side chain $R_1$. Although the dryness characteristics of the present compounds are influenced by the degree of unsat-uration of the side chain, preferred $R_1$ hydrocarbons contain no more than three unsaturated olefinic groups, even more preferably no more than two unsaturated olefinic groups and even more preferably no more than one unsaturated olefinic group. Thus, where $R_1$ is derived from oleic acid, the resulting compound generally exhibits a "dryer" feel when included in personal care products, than does stearic, linoleic is drier than oleic and linolenic is drier than linoleic when esterified with a monohydric aromatic alcohol such as benzyl alcohol or phenoxyethanol.

The present compounds may also function in personal care products in a dual nature, i.e., as dry emollients which have at least one additional characteristic or quality which is deemed to be beneficial in personal care products. For example, in addition to functioning as "dry emollients," the present compounds may also function as dispersants, gloss-enhancing agents, solubilizing agents, melting-point depressants, solvents for silicone fluids and lubricants in the cosmetic, toiletry and personal care industries. The presence of the fatty acid moiety portion of the present invention, although exhibiting a "dry" feel, still permits a desirable moisture balance as it softens and soothes the skin and related mucous membranes. This is an unexpected result.

Furthermore, it has been found that the compounds of the present invention are superior to other non-aromatic esters make them superior to existing non-monohydric aromatic alcohol containing esters which may include:

Water-White Color

Extremely Low Order of Eye/Skin Irritation

Low Order of $LD_{50}$

Excellent Compatibility in Cosmetic/Toiletry/Personal Care Formulations

Excellent Solvents for Sunscreens

Excellent Solvents for Silicones

Soluble in Most Alcohols

Soluble in Most Glycols

Soluble in Mineral Oils

Soluble in Petrolatum

Essentially Odorless

Excellent Dispersant for Inorganic Sunblocks

Demonstrates Proven Ability to Raise UV Absorbing Properties of Organic Sunscreens Esters of the present invention may be used in the cosmetic, personal care and toiletry compositions in amounts ranging from 0.05% to about 50% by weight, preferably about 0.5% to 25% by weight, more preferably from about 1.0% to about 20% by weight of the personal care, cosmetic or toiletry composition. The type and amount of the present compound which is added to end-use compositions will vary according to the type of composition and desired characteristics of the end-use composition.

In addition to the above-described characteristics, monohydric aromatic esters according to the present invention also assist in raising the SPF values of sunscreen formulations as well as functioning as dispersants for inorganic sunblocks well known in the art such as titanium dioxide and zinc oxide, among others. This is an unexpected result.

DETAILED DESCRIPTION OF THE INVENTION

The term "carboxylic acid" is used throughout the entire specification to describe a linear, cyclic, aromatic, or branched chain $C_{12}$ to $C_{20}$ hydrocarbon having a single carboxylic group at the terminus or at a position within the hydrocarbon rendering it an iso-acid (such that $R_1$ is a branched hydrocarbon group). Further, the monocarboxylic fatty acid may be fully saturated or contain one or more ethylenic groups. Exemplary monocarboxylic acids finding use in the present invention include, for example, dodecanoic or lauric, tridecanoic, tetradecanoic or myristic, pentadecanoic, isolauric, myristic, hexadecanoic or palmitic, oleic, linoleic, linolenic, octadecanoic or stearic, aradonic, behenic, erucic, isostearic and isoerucic acid. Further, alpha hydroxy acids as well as beta-hydroxy acids also find use in the present invention.

The term monohydric aromatic alcohol is used throughout the specification refers to such alcohols as benzyl alcohol, which may be produced by the oxidation of toluene or by dehalogenation of benzyl chloride making certain that impurities such as dibenzyl ether or benzaldehyde or dibenzaladeyde are removed by fractionation or chemical reduction to ensure a pure grade of benzyl alcohol that would be suitable for use in the cosmetic, toiletry or personal care industries. In addition, cinnamalcohol (reduced cinnamaldehyde) and anisyl alcohol may also be used in the present invention as well as alkyl substituted benzyl alcohol.

The term "emollient" is used throughout the specification to describe compounds according to the present invention which soften, lubricate and moisturize the skin as well as soothe irritation to the skin and mucous membranes. The term "dry emollient" is used throughout the present specification to describe the present invention which soften, lubricate, moisturize the skin, but do so without exhibiting oiliness, greasiness, tackiness, etc. (a substantial absence of same), which is often linked with "excessive" emolliency.

The term "emollient effective amount" is used throughout the specification to describe concentrations or amounts of compounds of the present invention which are included in cosmetic, toiletry and personal care formulations according to the present invention which provide "dry effective emollient" character for treating keratinous and epithelial tissue, including skin, hair and nasal passages. Compounds of the present invention may be used in the cosmetic, personal care and toiletry compositions in amounts ranging from about 0.05% to about 50% by weight, preferably about 0.5% to 25% by weight, more preferentially from about 1.0% to about 20% by weight of the personal care, cosmetic or toiletry composition.

The term "effective amount" is used throughout the present specifiction to describe concentrations or amounts of compounds according to the present invention which are effective in conveying desired traits such as dry emolliency and in certain preferred embodiments, at least one additional characteristic including emulsification, glossiness, "dry lubrication", melting point modification or solubility to a formulation of a cosmetic, toiletry or personal care product.

The term "unsubstituted" is used to describe a hydrocarbon moiety such as an alkyl, alkylene or related unsaturated group which contains only hydrogen atoms bonded to carbons with the moiety. The term "substituted" is used to describe a hydrocarbon moiety which contains a pendant hydroxyl group attached to a carbon atom of the moiety.

Compounds of the present invention may be prepared by synthetic methods known in the art. A general scheme involves reaction of at least one mole of a monohydric aromatic alcohol (purchased commercially or prepared using well known methods in the art) with at least one mole of a $C_{12}$–$C_{22}$ carboxylic acid, generally in the presence of an acid or base catalyst. Heat is applied to effect esterification and the water of esterification is removed. Heat is maintained until a suitable acid number is attained and the reaction mass is cooled, washed, neutralizred dried and distilled if necessary. The product should be essentially odorless, essentially water-white in color and contain a substantial absence of free fatty acid, residual catalyst or free alcohol. In essence, the product must be suitable for sale in the cosmetic, toiletry or pesonal care industry.

Compounds of the present invention may be used as emollients for the skin and epithelial tissue such as hair, ungual tissue (nails), skin and related mucous membranes. By addition of an emollient effective amount of the present compound, formulations for use as cosmetic, toiletry and personal care products will acquire a soothing and dry rather than an oily or greasy effect.

Effective amounts of the present compounds may also serve a dual function, for example, as gloss-producing agents for lipsticks and lip balm formulations in the personal care, cosmetic and toiletry industries as a substitute(s) for castor oil normally used in such formulations. The compounds of the present invention exhibit outstanding solubility characteristics for pigments used in lip products and are completely compatible with existing raw materials used in lip formulations such as castor oil, triglycerides of caprylic/capric acids, triglyceride of caprylic acid, mixtures of octyl isononanoate/diethylene glycol/dioctanonoate and dioctanoate/isodecyl octanoate, among others.

In addition, the present compounds have been found to enhance the SPF values of sunscreen formulations, in effect, synergizing the active UV absorber. For example, when incorporated into a specific sunscreen formulation at a level of 10% (with all aspects of the formulation remaining at the same level), it was noted that the SPF level was increased by a factor of 20% from a value of 25 (without the present compounds benzyl laurate/myristate/benzyl palmitate) to a value of 31.0 on the same individual. Similarly, in a sunscreen formulation with an anticipated or projected SPF value of 15 (actually evaluated at 12) the introduction of 10% by weight of benzyl laurate/myristate/palmitate, the SPF was increased to a value of 15 when the identical formulation was evaluated in specific studies on individuals with all ingredients remaining at the same concentration. This represents an actual increase of approximately 20% which appears to represent a similar increase in the projected SPF 25 formulation. One of ordinary skill will recognize to vary the componentry of compositions according to the present invention in order to enhance the SPF using compounds according to the present invention in sunscreen compositions or formulations.

In general, compounds according to the present invention are included in end-use formulations in amounts ranging from about 0.05% to about 50% by weight, more preferably about 0.50% to about 25% by weight, even more preferably about 0.1% to about 20% by weight, depending upon the end-use. Depending upon the end-use, personal care compositions according to the present invention may additionally comprise any one or more of water, solvents such as alcohol and isopropanol, conditioning agents, surfactants, emulsifiers, thickeners, coloring agents, preservatives, humectants, medicaments, fragrances, oils, suspending agents, UV absorbers and pigments.

The inclusion of the present compounds in shampoos, lotions and conditioers and other cosmetic, personal care and toiletry compositions may be used on the skin and hair in some circumstances to create a dry feel, thus avoiding a greasy or oily feel as is often the case in formulations employing linear and in some circumstances isomeric esters.

For example, in shampoos, rinses and conditioners, the compounds according to the present invention preferably comprise about 0.25% to about 20% by weight, more preferably about 0.25% to about 10% by weight of the final end-use hair-care composition. Other components which may be included in hair-care formulations include, for example, a solvent or diluent such as water and/or alcohol, surfactants or emulsifiers, thickeners, coloring agents, preservatives, conditioning agents and humectants, among numerous others.

In the case of shave creams and gels, after-shave lotions and shave-conditioning compositions (for example, pre-electric shave formulations), the compounds according to the present invention are included in amounts ranging from about 0.25% to about 15% or more by weight, more preferably about 0.5% to about 10% by weight. Other components which may be included in these end-use compositions include, for example, water, and at least one or more of emollients, humectants and emulsifiers, conditioning agents, medicaments, fragrances and preservatives.

In the case of skin lotions and creams, the present compounds are included in amounts ranging from about 0.25% to about 25% by weight, more preferably, about 0.5 to about 10% by weight. Additional components which may be employed in these compositions include, for example, water, additional emollients, emulsifers, oils, conditioning agents, medicaments, fragrances and preservatives.

In the case of sunscreens and skin-protective compositions, the present compounds are included in amounts ranging from about 0.25% to about 20% or more by weight, preferably about 0.5% to about 7.5% by weight of the final formulations. Additional components which may be employed in these compositions may include, for example, a UV absorbing composition such as para-amino benzoic acid (PABA) or a related UV absorber or a pigment such as $TiO_2$ or ZnO, water or oil, and optional components including, for example, one or more of an oil, water, suspending or dispersing agents, conditioning agents and emollients, among others.

In providing skin protective or sunscreen compositions according to the present invention, it is preferred that a dispersion be formed between ground or milled (preferably, micronized) pigment such as $TiO_2$ or ZnO and one or more of the compounds according to the present invention, the weight ratio of pigment to ester compound falling within the range of about 5:95 to about 50:50, with a preferred ratio being about 30:70 pigment to present ester compound on a weight/weight basis. One or more dispersing or suspending agents may also be added to this dispersion The dispersion may be advantageously formed by adding the pigment to the emollient ester compound, which also serves as an SPF booster because of its ability to spread the pigment after application of the sunscreen composition on the skin. The dispersion prepared above is then advantageously added to other components to make the final sunscreen or skin protective composition.

While not being limited by way of theory, it is believed that the present compounds exhibit superior solubility characteristics of sunscreen compounds which are in common use including octyl methoxy cinnamate, octyl salicylate, 2-ethylhexyl ester of p-dimethylamino benzoic acid, and octacrylene enable the active sunscreens to more evenly spread over the skin, thereby yielding an increase in SPF values. Listed below are formulations which have been evaluated and used as the basis for the above-described study.

In addition to serving as SPF enhancers of organic sunscreen compounds, the present compounds also serve as excellent dispersants and coating agents for inorganic pigments (sunblocks) such as titanium dioxide and zinc oxide. Recently, there has been an increasing trend to replace organic UV absorbers with sunblocks because of potential irritation problems encountered in a percentage of sunscreen users. It has been unexpectedly been found that by increasing the molecular weights of the present invention, for example, by using 12-hydroxy stearic acid or ricinoleic acid or erusic acid derivatives, it has been found that the same level of stability and prevention of agglomeration of pigments can be obtained, and in some instances, better stability than is obtainable through the use of dispersants such as glyceryl tricaprylate, caprate esters, octadecyl neopentanoate, isopropyl myristate, etc. Furthermore, it is possible to employ compounds of the present invention in sunscreen formulations employing both active (organic) LTV absorbers as well as (sunblocks) inorganic micronized pigments such as titanium dioxide and zinc oxide, thus obtaining formulation ease and compatability as well as unexpectedly enhanced SPF values.

In the case of lipsticks and lip balm compositions, the present compounds are included in amounts ranging from about 0.5% to about 20% by weight, more preferably about 0.5% to about 10% by weight of the final formulations. Additional components which may be added to lipstick and lip balm compositions include waxes such as ozokerite, beeswax, candelia wax and carnauba wax, oils such as mineral oil and petrolatum, binders (solvents) such as castor oil, glyceryl monooleate, lanolin and isopropyl palmitate, isopropyl lanolate and isopropyl myristate, thickeners, such as bentone gels, pigments, preservatives, flavoring agents and coloring agents.

The compounds of the present invention permit a wide degree of formulation flexibility in the preparation of personal care, toiletry and cosmetic finished goods. By selecting esters of the present invention synthesized from lower molecular weight acids, for example, $C_{12}$, $C_{14}$ and $C_{16}$, one can achieve a "dryness" in final formulations which find use in the cosmetic, toiletry and pesonal care area. Similarly, it is possible to achieve "dryness" using higher molecular weight acids such as oleic, linoleic, linolenic or ricinoleic acid (these are all $C_{18}$ fatty acids containing one or more unsaturated double bonds which are either unsubstituted or contain hydroxyl substitution, as in the case of oleic acid and ricinoleic acid) which retain their "dry" characteristizcs as a result of their molecular unsaturation (at least one unsaturated carbon=carbon double bond) yet obtain higher viscosities in finished goods sold in the cosmetic, toiletry and personal care area because of the increased weight.

Furthermore, increased or higher molecular weight esters of the present invention continue to exhibit liquidity at ambient temperatures and still impart "dryness" in their emolliency when incorporated into finished goods when used for personal care, cosmetic and toiletry products.

The compounds of the present invention permit a wide degree of formulation flexibility in the preparation of goods sold to the personal care, toiletry and cosmetic marketplace. By selecting compounds of the present invention derived from decanoic, lauric, myristic and/or palmitic acids, it is possible for the formulator to achieve "dryness" with emolliency and decreased viscosity. On the other hand, by selecting fatty acids of higher molecular weight which are isomeric or contain pendant hydroxyl groups, for example, isostearic acid or 12-hydroxystearic acid, it is still possible to maintain "dryness" in a given formulation and still control viscosity of the finished product.

It has been further found with the compounds of the present invention that "dryness" is also effected by the degree of unsaturation that may be present in a given molecular. In other words, the length of the fatty acid side chain is one factor which affects "dryness" with the secondary factor being attributed by the degree of unsaturation, with greater unsaturation being responsible for dryness at a higher molecular weight, for example, when the fatty acid used to make the esters is a $C_{16}$–$C_{22}$ fatty acid. It has been noted that an oleic acid derivative of the present invention exhibits more "dryness" than the stearic acid derivative and that the linoleic acid derivative exhibits more "dryness" than the oleic acid derivative and continuing with added unsaturation, the linoleyl acid derivative of a corresponding compound of the present invention exhibits more "dryness" than the linoleic acid derivative.

It has been noted that with an increase in the corresponding chain length of a given fatty acid moiety of the present invention, the characteristics of water repellency has been increased. Therefore, by controlling or properly selecting the molecular weight of the compounds of the present invention, it is possible to increase "water repellency" and thereby enhance the effectiveness of a given formulation used in the cosmetic, toiletry or personal care industry, even with increased dry emolliency.

In addition, those emollient compositions which produce a water repellent barrier, also result in a vapor barrier, which enhances the loss of water from epithelial tissue, thus producing a "plumpness" of the skin. The advantage of this aspect of the present invention lies in promoting an anti-aging look with an impact on wrinkled skin, an unexpected result.

The ideal properties of emolliency of compounds of the present invention result from utilizing fatty acids from 12 to 22 carbons in length, wherein their fatty acid moiety can be either saturated, unsaturated, branched, or isomeric and may contain pendant hydroxy groups. The higher the degree of unsaturation in the selection of the fatty acid moiety in compounds of the present invention tends to maintain the "dryness" of finished goods into which these esters have been incorporated.

The following examples of compounds relating to the present invention have been prepared:

Benzyl Behenate
Benzyl Hydroxystearate
Benzyl Isostearate
Benzyl Ricinoleate
Benzyl Erucate
Benzyl Laurate
Benzyl Myristate
Benzyl Palmitate
Benzyl Stearate
Benzyl Laurate/Myristate/Palmitate
Benzyl Arichidonate
Benzyl Linolenate
Benzyl Linoleate
Benzyl Oleate
Phenoxyethyl Arichidonate
Phenoxyethyl Laurate
Phenoxyethyl Stearate
Phenoxyethyl Laurate/Myristate/Palmitate
Phenoxyethyl Erucate
Phenoxyethyl Linolenate
Phenoxyethyl Linoleate Phenoxyethyl Oleate The present invention is now described, purely by way of illustration, in the following examples. It will be understood by anyone of ordinary skills in the art that these examples are in no way limiting and that variations of detail can be made without departing from the spirit and scope of the present invention.

Manufacturing Procedure

Synthesis of Benzyl Laurate/Myristate/Palmitate

Into a clean and dry reactor benzyl alcohol (1.26 mole ratio) was added to a mixture of palmitic acid, myristic acid and lauric acid (at mole ratios of 0.15/0.15/0.7 respectively). Nitrogen is charged to the flask and the flask was heated to 60–70° C. to melt the fatty acids. When the batch is a liquid the catalyst (methanesulfonic acid 70% in methanol) is added to the mixture (about 0.29% by weight). The temperature is then raised slowly to 160° C. distilling off water and refluxing benzyl alcohol. When the distillation either stops or slows considerably, apply vacuum slowly to approximately 30". Maintain the conditions of heat and vacuum. When distillation of the water of reaction and residual benzyl alcohol slows appreciably or stops, sample to laboratory. The test acid vlaud should be a maximum of 3.0. When the acid value is a maximum of 3.0, the batch should be cooled to 70–80° C. and the vacuum should be released. The acid value of the sample is again tested. The batch is then neutralized with a solution of caustic potash-45 (45% potassium hydroxide—prepared from the acid value times the wt of the batch/1000) in an amount equal to about 10% by weight of the batch. The potash mixture is added to the batch, mixed at 70–80° C. for about 5 minutes. The agitator is then turned off and the batch is sampled after the water layer is removed. When the acid value of the sample is a maximum of 0.2, an amount of sodium sulfite or bisulfite (about 0.2% by weight of the sample) pre-mixed in water is added to the batch. The batch is washed three times and tested for acid value (0.2 maximum). A sample of the batch is then dried in a flask to 120° C., cooled and then tested to make certain that the appearance of the sample is clear, the color is within limits (APHA no greater than 100) and the odor is acceptable. Thereafter, the product is steam distilled at 100–120° C. Each hour the sample is compared to a standard. Dry the batch at 120° C. and 30" vacuum. Cool to 25–40° C. and sample. If sample meets the following criteria: clear appearance, color APHA (100 maximum) and the acid value is a maximum of 0.2, then unload batch for use in final products.

Other ester compounds according to the present invention may be prepared readily with minor variation to the above-described scheme.

EXAMPLES

Example 1

SPF 15 Sunscreen Formulations

| | SPF 15 % By Weight | INGREDIENT | SPF 15 Present Invention % By Weight |
|---|---|---|---|
| A | 7.50 | Octylmethoxy Cinnamate | 7.50 |
| | 3.00 | Octyl Salicylate | 3.00 |
| | 3.00 | Benzophenone-3 | 3.00 |
| B | 1.00 | Laureth-16 and Ceteth-16 and Oleth-16 and Steareth-16 | 1.00 |
| | 3.00 | Cetyl Alcohol | 3.00 |
| | 2.50 | Glycerol Monostearate and PEG-100 Stearate | 2.50 |
| C | 1.00 | Silicone 350 | 1.00 |
| | 8.00 | $C_{12}$–$C_{15}$ benzoate | — |
| | 8.00 | Isocetyl Stearate | 6.00 |
| | 1.00 | $C_{12}$–$C_{15}$ Benzoate Esters | 1.00 |
| | 2.00 | Sepigel 305 | 3.00 |
| | — | Benzyl Laurate/Myristate/Palmitate | 10.00 |
| D | 60.00 | $H_2O$, Dionized | 59.00 |
| | 100.00 | | 100.00 |

Procedure: Heat A to 60° C. Heat B to 60° C. Combine A and B at 60° C. Heat part C to 60° C. Combine part C with the A-B mixture, add water and cool

Example 2

SPF 30 Sunscreen Formulations

| | SPF 30 % By Weight | INGREDIENT | SPF 30 Present Invention % By Weight |
|---|---|---|---|
| A | 7.50 | Parsol MCX | 7.50 |
| | 3.00 | Octyl Salicylate | 3.00 |
| | 3.00 | Benzophenone-3 | 3.00 |
| | 1.00 | Solulan-16 | 1.00 |
| B | 2.50 | Cetyl Alcohol | 3.00 |
| | 2.50 | Arlacel-165 | 2.50 |
| | 1.00 | Silicone-350 | 1.00 |
| | — | Benzyl Laurate/Myristate/Palmitate | 10.00 |
| | 8.00 | Isocetyl Stearate | — |
| | 1.00 | Germaben-11E | 1.00 |
| | 2.50 | Sepigel-350 | 2.50 |
| | 54.50 | Water, Dionized | 52.50 |
| C | 5.00 | $TiO_2$ Micronized | 5.00 |
| | 8.00 | $C_{12}$–$C_{15}$ Benzoate | 8.00 |
| | 100.00 | | 100.00 |

Procedure: Heat A to 60° C. Heat B to 60° C. Combine A and B at 60° C. Heat part C to 60° C. Combine part C with the A-B mixture, add water and cool

Example 3

Moisturizing After Shave Treatment with "Dry" Afterfeel

| | INGREDIENTS | %, WEIGHT |
|---|---|---|
| A. | Glyceryl Stearate (and) Cetereth-20 (and) Cetereth-10 (and( ) Cetearyl Alcohol (and) Cetyl Palmitate | 6.00 |
| | Cetearyl Alcohol | 1.00 |
| | Benzyl Laurate/Myristate/Palmitate | 8.00 |

-continued

| | INGREDIENTS | %, WEIGHT |
|---|---|---|
| | Octyldodecanol | 4.00 |
| B. | Water (Deionized) | q.s. |
| | Glycerin | 3.00 |
| | Phenoxyethanol (and) Methyl Paraben (and) Butyl Paraben (and) Ethyl Paraben (and) Propyl Paraben | 0.5 |
| | Carbomer 10 | 0.3 |
| C. | Triethanolamine | q.s. |
| D. | Bisabolol | 0.2 |
| | Alcohol | 3.00 |
| | Sodium Hyaluranate (and) Wheat Germ Extract (and) Aracharomyces Cerevisiae Extract | 4.00 |
| | | 100.00 |

Procedure:
1. Heat A to 80° C.
2. Disperse the Carbomer, then heat to 75° C. the rest of B.
3. With stirring, add B to A; cool to 50° C.
4. Homogenize and cool to 30° C. Adjust pH to 5.7 with C.
5. Add D in sequence and stir until cold.

Example 4

Alcohol Free After Shave with "Dry" Feel

| | INGREDIENTS | %, WEIGHT |
|---|---|---|
| A. | Water (Deionized) | q.s. |
| | Diglycerol | 10.00 |
| | Phenoxyethanol | 0.5 |
| | Allantoin | 0.1 |
| | Imidazolinidinyl Urea | 0.2 |
| | Wheat Germ Triglyceride[1] | 3.00 |
| | Glycereth 4.5 Lactate[1] | 2.00 |
| | Carbomer (Carbopol 980) | 0.20 |
| B. | Benzyl Ricinoleate | 3.00 |
| | PEG-20 Methyl Glucose Sesquistearate | 1.00 |
| C. | Triethanolamine | 0.2 |
| | | 100.00 |

[1]Available from ALZO INC., Sayreville, New Jersey

Procedure:
1. Dissolve A in Water and heat to 60° C.
2. Heat B to 60° C.
3. With stirring, add B to A.
4. Homogenize and cool to room temperature.
5. Neutralize with C.
6. Stir until cool.

Example 5

"Dry" Feel Gel for Regenerative Care

| | INGREDIENTS | %, WEIGHT |
|---|---|---|
| A. | Glycerine (and) Glyceryl Polyacrylate | 20.00 |
| | Water (Deionized) | 35.70 |
| | Xanthan Gum, 1% aq. Solution | 30.00 |
| | Phenoxyethanol (and) Methyl Paraben (and) Butyl Paraben (and) Ethyl Paraben (and) Propyl Paraben | 0.3 |
| | Benzyl Laurate/Myristate/Palmitate | 4.00 |
| B. | Glucereth-7-Lactate | 0.5 |

-continued

| | INGREDIENTS | %, WEIGHT |
|---|---|---|
| | Na3-Citrate, Anhydrous | 0.14 |
| | Water (Deionized) | 9.36 |
| | | 100.00 |

Procedure:

1. Mix A at room temperature; bring pH to 7.0 with NaOH.
2. Dissolve B at room temperature and add to A with stirring.
3. Add fragrance.

Example 6

Gel for Problem Skin Control with Dry Afterfeel

| | INGREDIENTS | %, WEIGHT |
|---|---|---|
| A. | Water (Deionized) | 65.00 |
| | Phenoxyethanol (and) Methyl Paraben (and) Butyl Paraben (and) Ethyl Paraben (and) Propyl Paraben | 0.5 |
| | Xanthan Gum | 0.5 |
| | Benzyl Linoleate | 4.00 |
| | Cyclodextrin (and) Tea Tree Oil | 5.00 |
| B. | Glyceryl Polymethacrylate (and) Propylene Glycol | 25.00 |
| | | 100.00 |

Procedure:

1. Disperse A at room temperature and stir into B.
2. Add fragrance and homogenize.

Example 7

Concentrated Gel with Dry Afterfeel

| | INGREDIENTS | %, WEIGHT |
|---|---|---|
| A. | Caprylic/Capric Triglyceride | 33.8 |
| | Tocopheryl Acetate | 0.1 |
| B. | Butyl Paraben | 0.1 |
| | Benzyl-12-Hydroxystearate | 25.00 |
| | Cetyl Alcohol | 8.00 |
| | Hydrogenated Lanolin | 20.00 |
| | Hydroxy Trimethyl Silane (and) Stearyl Alcohol | 3.00 |
| C. | Octyldodecanol (and) Lecithin (and) Arachidyl Propionate (and) Tocopheryl Acetate (and) Retinyl Palmitate (and) Linoleic Acid (and) Linolenic Acid | 10.00 |
| | | 100.00 |

Procedure:

1. Heat A to 80° C.
2. With stirring, add B until completely homogenized.
3. With gentle stirring at room temperature, cool to 50° C.

Example 8

Hair Gel for Gloss

|   | INGREDIENTS | %, WEIGHT |
|---|---|---|
| A. | Petrolatum | 79.45 |
|   | Glucereth-7-(120-Hydroxy Stearate/ IPDI Copolymer[1] | 5.00 |
| B. | Castor Oil/IPDI Copolymer[1] | 4.75 |
|   | Benzyl Ricinoleate | 10.00 |
| C. | Vitamin E Acetate | 0.1 |
| D. | Fragrance | 0.2 |
| E. | Color | q.s. |
|   |   | 100.00 |

Procedure:
1. Heat A to 65° C.
2. Add B, C, D and E; mix uniformly after each addition.
3. Pour at 55° C.

Example 9

Facial Scrub with Dry Afterfeel

|   | INGREDIENTS | %, WEIGHT |
|---|---|---|
| A. | Carbomer 940 | 0.20 |
| B. | Water (Deionized) | 63.5 |
|   | Glyerceth-7-Glycolate[1] | 2.00 |
| C. | Glyceryl Stearate (and) PEG-100 | 6.00 |
|   | Diethylene Glycol Adipate/IPDI Copolymer[1] | 5.00 |
|   | Benzyl Laurate/Myristate/Palmitate | 8.00 |
|   | Triple Pressed Stearic Acid | 3.00 |
|   | Stearyl Alcohol | 1.00 |
| D. | Triethanolamine, 99% | 0.3 |
| E. | Propylene Glycol (and) Diazolidinyl Urea (and) Methyl Paraben (and) Propyl Paraben | 1.00 |
| F. | Polyethylene Micro Paraben | 1.00 |
| F. | Polyethylene Micro Powders | 1.00 |
|   |   | 100.00 |

[1]Alzo, Inc.

Procedure:
1. Very slowly, sprinkle A into B. Add the powder into a vortrex.
2. Stir until uniform dispersion; heat to 65° C.
3. Heat C in separate container to 70° C.
4. Add C at 70° C. to A,B at 65° C.
5. Mix a few minutes, then add D with slow stirring.
6. Begin cooling to room temperature.
7. At 55° C., add E and F.
8. Add cold water, quantity sufficient.

Example 10

Hard Skin Remover with Dry Afterfeel

|   | INGREDIENTS | %, WEIGHT |
|---|---|---|
| A. | Benzyl Oleate | 3.00 |
|   | Triple Pressed Stearic Acid | 5.00 |
|   | Hydrogenated Castor Oil/IPDI Copolymer | 8.00 |
|   | Cetearyl Alcohol | 1.00 |
|   | Ceteareth-20 | 2.00 |

-continued

|   | INGREDIENTS | %, WEIGHT |
|---|---|---|
|   | Propyl Paraben | 0.05 |
|   | Polyderm PPI-SI-50 | 5.00 |
| B. | Water (Deionized) | 67.24 |
|   | Methyl Paraben | 0.15 |
| C. | Tea Tree Oil | 0.1 |
|   | Peppermint Oil | 0.1 |
|   | Menthol Crystals | 0.2 |
|   | Water (Deionized) and C.S. FD & C Blue No. 1, 1% Solution | 0.08 |
|   | Polyethylene Beads | 8.00 |

Procedure:
1. Heat B to 70° C.
2. Heat B to 70° C.
3. Add the Silicone/IPDI Copolymer, merging the two phases.
4. Add B to A, with high shear.
5. After 5 minutes' mixing, change to anchor-type mixer, and mix slowly.
6. While cooling, add the essentials oils, Menthol and color, when below 35° C.
7. Finally, stir in the Polyethylene.

Example 11

Non-chemical Sunscreen Lotion (Approx. SPF 15)

This lotion incorporates Titanium Dioxide as the sunscreen agent. It has a smooth feel upon application and rubs in easily without whitening. The Phase B ingredients add thickness and are believed to contribute to water resistance and product stability.

|   | INGREDIENT | %, WEIGHT |
|---|---|---|
| A. | Water (Deionized) | 64.80 |
|   | Magnesium Aluminum Silicate | 0.80 |
|   | Xanthan Gum | 0.25 |
|   | Methylparaben | 0.20 |
|   | Tetrasodium EDTA | 0.10 |
| B. | Mineral Oil (and) Hydrogenated Butylene/ Ethylene/Styrene Copolymer (and) Hydrogenated Ethylene/Propylene/Styrene Copolymer | 10.00 |
| C. | Benzyl Laurate/Myristate/Palmitate | 10.00 |
|   | Titanium Dioxide | 6.00 |
|   | Phenoxyethanol | 0.70 |
|   | Stearic Acid | 2.50 |
|   | Glyceryl Stearate SE | 2.00 |
|   | DEA-Cetyl Phosphate | 2.50 |
|   | Propylparaben | 0.10 |
| C. | Fragrance | 0.05 |
|   |   | 100.00 |

Procedure:
1. Disperse Magnesium Aluminum Silicate in rapidly agitated deionized water. Mix well. Add Xanthan Gum.
2. Mix until uniform. Heat to 80° C.
3. Add remaining Phase A ingredients.
4. Homogenize BL/M/P and Titanium Dioxide until smooth.
5. Add remaining Phase B ingredinets. Heat to 80–85° C. Mix until all the solids are completely dissolved.
6. Add Phase B to Phase A while mixing with good agitation. Mix for 30 minutes until homogeneous.
7. Cool to 40° C.
8. Add Phase C. Continue mixing and cooling to 30° C.

Example 12

Roll-on Lip Gloss

| INGREDIENTS | %, WEIGHT |
| --- | --- |
| Benzyl Ricinoleate | 7.00 |
| Arichidyl Propionate | 3.00 |
| Lanolin Oil | 50.00 |
| Polybutene | 25.00 |
| Propylene Glcyol Monoisostearate | 10.00 |
| Fragrance | 5.00 |
| Colorant, Preservative | q.s. |
| | 100.00 |

Procedure:
Heat and mix all ingredients until a uniform mixture is obtained.

Example 12

Sunscreen Gel (Approx. SPF 12)

A clear sunscreen gel with excellent spreadability and a pleasant, emollient after feel. Phase A provides viscosity, lubricity and water repellency to this formula.

| | INGREDIENTS | %, WEIGHT |
| --- | --- | --- |
| A. | Mineral Oil (and) Hydrogenated Butylene/Ethylene/Styrene Copolymer (and) Hydrogenated Ethylene/Propylene/Styrene Copolymer | 65.00 |
| | Benzyl Linoleate | 20.80 |
| | Tocopheryl Acetate | 0.50 |
| | Fragrance | 0.10 |
| C. | Octyl Methoxycinnamate | 7.50 |
| | Benzophenone-3 | 4.00 |
| | Octyl Salicylate | 2.00 |
| | Propylparaben | 0.10 |
| C. | D & C Red No. 4 Aluminum Lake | q.s. |
| | | 100.00 |

Procedure:
1. Mix A until homogeneous.
2. Heat B to 60° C. until clear.
3. Add B to A with moderate mixing.
4. Add C as necessary.

Example 13

High SPF Sunscreen Lotion

| | INGREDIENT | %, WEIGHT |
| --- | --- | --- |
| A. | Water (Deionized) | 72.1 |
| | Acrylates/C10–30 Alkyl Acrylate Crosspolymer | 0.2 |
| | Propylene Glycol | 3.0 |
| B. | Stearic Acid | 3.0 |
| | Glyceryl Stearate (and) PEG-100 Stearate | 2.0 |
| | Stearyl Alcohol | 1.0 |
| | Octyl Methoxycinnamate | 7.0 |
| | Octyl Salicylate | 2.0 |
| | Benzephenone-3 | 3.0 |
| | Titanium Dioxide | 1.0 |

-continued

| | INGREDIENT | %, WEIGHT |
| --- | --- | --- |
| | Benzyl Isostearate | 2.0 |
| C. | Triethanolamine | 0.5 |
| D. | Cyclomethicone (and) Dimethiconol | 3.0 |
| E. | DMDM Hydantoin | 0.2 |

Procedure:
1. While heating water to 70° C. (158° F.), slowly sift in Acrylates/C10–30 Alkyl Acrylate Crosspolymer. Add the rest of Phase A and mix until uniform.
2. Combine Phase B ingredients; heat to 70° C. (158° F.); mix until clear.
3. Add Phase B to Phase A slowly with turbulent mixing; begin cooling
4. Add Phase C; mix well.
5. Add Phase D; mix well.
6. Add Phase E; mix well while cooling to room temperature.

| TYPICAL PROPERTIES: | |
| --- | --- |
| Viscocity, RVT @ 2.5 rpm, 30 sec, cp | 3000 |
| Stability, @ 40° C. (104° F.) months | 3 |
| pH | 6.5 |

Example 14

Perfumed Body Lotion

This creamy body lotion rubs in easily and relieves dryness. Skin is left feeling soft, smooth and mositurized. Mineral Oil (and) Hydrogenated Butylene/Ethylene/Styrene Copolymer (and) Hydrogenated Ethylene/Propylene/Styrene Copolymer enhances the richness and moisturizing properrties of this lotion.

| | INGREDIENT | %, WEIGHT |
| --- | --- | --- |
| A. | Water (Deionized | 67.20 |
| | Carbomer | 0.20 |
| | Propylene Glycol | 7.00 |
| | Methylparben | 0.20 |
| | Panthenol | 0.10 |
| B. | Mineral Oil (and) Hydrogenated Butylene/Ethylene/Styrene Copolymer (and) Hydrogenated Ethylene/Propylene/Styrene Copolymer | 7.00 |
| | Benzyl Oleate | 7.00 |
| | Isostearyl Alcohol | 2.00 |
| | Propylparaben | 0.10 |
| | Cetyl Alcohol | 2.00 |
| | Glyceryl Stearate (and) PEG-100 Stearate | 2.50 |
| | Dimethicone | 0.50 |
| | Potassium Cetyl Phosphate | 1.75 |
| | Tocpheryl Acetate | 0.10 |
| C. | Triethanolamine, 99% | 0.15 |
| D. | Diazolidinyl Urea | 0.20 |
| E. | Soy Lecithin | 1.00 |
| | Fragrance | 1.00 |
| | | 100.00 |

Procedure:
1. Disperse Carbomer into rapidly agitated deionized water. Add remaining Phase A ingredients.
2. Heat to 75–80° C. and mix until uniform and lump-free.

3. Combine Phase B. Heat to 80° C. and mix until all the solids are dissolved.
4. Add Phase B to Phase A. Mix for 30 minutes with good agitation.
5. Add Phase C. Mix until completely smooth and homogeneous. Cool to 50° C.
6. Add Phase D. Cool to 40° C.
7. Add Phase E. Continue mixing and cooling to 30° C.

Example 15

Lipstick Base

| INGREDIENT | %, WEIGHT |
|---|---|
| Castor Oil | 42.60 |
| Benzyl Laurate/Myristate/Palmitate | 19.00 |
| Candelilla Wax | 16.00 |
| Arichidyl Propionate | 0.5 |
| Petrolatum | 11.5 |
| Lanolin | 5.0 |
| Ozokerite | 2.5 |
| Castor Oil/IPDI Copolymer | 1.0 |
| Carnauba | 1.0 |
| Beeswax | 0.5 |
| Propylparaben | 0.10 |
| Aloe Extract | 0.10 |
| Propyl Gallate | 0.10 |
| Tocopheryl Acetate | .10 |
|  | 100.00 |

Example 16

Low SPF Sunscreen Oil

| | INGREDIENT | %, WEIGHT |
|---|---|---|
| A. | Polyisobutene | 10.0 |
| | Mineral Oil | 10.0 |
| | Octyl Salicylate | 3.0 |
| | Stearyl Dimethicone | 1.0 |
| B. | Octyldodecyl Behenate Benzyl Laurate | 0.5 |
| | Benzyl Laurate/Myristate/Palmitate | 5.5 |
| | Cyclomethicone | 70.0 |
| | | 100.0 |

Procedure:
1. Combine Phase A ingredients in order; heat to 50° C.; mix until uniform.
2. Begin cooling to room temperature while mixing; add Phase B ingredients in order; mix until homogeneous.

Typical Properties:
Viscosity . . . Low; suitable for non-aerosol pump spray
Stability, @ 40° C., months . . . 1

Example 17

Medium SPF Sunscreen

| | INGREDIENT | %, WEIGHT |
|---|---|---|
| A. | Lauryl Methicone Copolyol | 2.0 |
| | Mineral Oil | 10.0 |

-continued

| | INGREDIENT | %, WEIGHT |
|---|---|---|
| | Octylmethoxy Cinnamate | 5.0 |
| | Octyl Salicylate | 2.0 |
| | Benzophenone-3 | 1.0 |
| | Titanium Dioxide | 1.0 |
| | Benzyl Laurate/Myristate/Palmitate | 3.0 |
| B. | Cyclomethicone | 6.0 |
| C. | Water (Deionized) | 68.3 |
| | NaCl | 1.0 |
| | Polysorbate 20 | 0.5 |
| D. | DMDM Hydantoin | 0.2 |
| | | 100.0 |

Procedure:
1. Combine Phase A ingredients in order; heat to 70° C.; mix until uniform.
2. Add Phase B after Phase A has been heated to avoid prolonged heat and evaporation of the volatile silicone.
3. Combine Phase C ingredients; heat to 70° C.; mix until clear.
4. Add Phase C to Phase B VERY SLOWLY with turbulent mixing.
5. Begin cooling to room temperature while mixing and add Phase D.
6. For more uniform particle size of the internal phase, a finishing homogenization step may be used.

Typical Properties:
Viscosity, RVT-C @ 2.5 rpm, 30 sec, cp . . . –60,000
Stability @ 40° C., months . . . 1

Biological Studies

Skin Irritation Studies

Eye Irritation Study of Benzyl Linoleate

The test procedure employed is described in the *Appraisal of the Safety of Chemicals in Foods, Drugs and Cosmetics*, published by the Association of Food and Drug Officials of the United States. Nine normal healthy albino rabbits were used for this study.

Each of the nine animals had 0.1 ml of the test material (benzyl linoleate) instilled into one eye of each test animal. The other eye was untreated and observed as a control. Two seconds after instillation of the test material, a washout was conducted in 3 of the rabbits using 20 ml. of warm water. Four seconds after test material instillation, washout was conducted in 3 additional rabbits using 20 ml. of warm water. All animals were examined frequently during the seven following days.

The sample of benzyl linoleate, tested as indicated above, produced no irritation in rabbit eyes. According to the reference, the material may be considered non-irritating.

Dermal Irritation Study of Benzyl Linoleate

The test procedure employed is described as Local Toxicity, Primary Irritation of the Skin in "Appraisal of the Safety of Chemicals in Foods, Drugs and Cosmetics" published by the Food & Drug Officials of the United States.

The dose to test the response was 0.5 ml/patch with 4 patches on each of 6 rabbits. The results indicated a primary skin irritation index of 2.375. The material was considered a moderate irritant in this test system.

Oral $LD_{50}$ of Benzyl Linoleate in Rats

The test procedure employed is described in the "Appraisal of the Safety of Chemicals in Foods, Drugs and Cosmetics" published by the Food & Drug Officials of the United States.

Oral $LD_{50}$ was determined to be 7.0 ml/kg. A summary of gross autopsy findings on dead animals showed hemorrhagic lungs, dark livers and spleens, slight hemorrhagic stomachs and intestines and pale kidneys. All other organs were unremarkable.

It is understood by those skilled in the art that the foregoing description and examples are illustrative of practicing the present invention, but in no way limiting. Variations in the detail presented herein may be made with departure from the spirit and scope of the present invention as defined by the following claims:

What is claimed is:

1. A method of enhancing the dry emolliency of a cosmetic, toiletry or personal care composition comprising components selected from the group consisting of water, solvents, conditioning agents, surfactants, emulsifiers, thickeners, coloring agents, preservatives, humectants, medicaments, fragrances, oils, suspending or dispersing agents, UV absorbers and pigments, said method comprising adding to said composition an effective amount of a compound according to the structure:

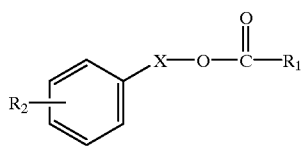

wherein
   $R_1$ is a $C_{17}$ to $C_{21}$ unsaturated hydrocarbon group which is linear or branched and is unsubstituted or substituted with a pendant hydroxyl group;
   X is $CH_2$, $OCH_2CH_2$ or $HC=CHCH_2$;
   and $R_2$ is H, $OCH_3$, $CH_3$ or $CH_2CH_3$.

2. The method according to claim 1 wherein $R_1$ contains at least two unsaturated carbon-carbon bonds.

3. The method according to claim 1 wherein X is $CH_2$ and $R_2$ is H.

4. The method according to claim 1 wherein $R_1$ contains at least one pendant hydroxyl group, X is $CH_2$ and $R_2$ is H.

5. A method of enhancing dry emolliency and at least one additional characteristic of a cosmetic, toiletry or personal care composition selected from the group consisting of solvency, gloss and melting-point depression, said composition consisting essentially of components selected from the group consisting of water, solvents, conditioning agents, surfactants, emulsifiers, thickeners, coloring agents, preservatives, humectants, medicaments, fragrances, oils, suspending agents, UV absorbers and pigments, said method comprising adding to said composition an effective amount of a compound according to the structure:

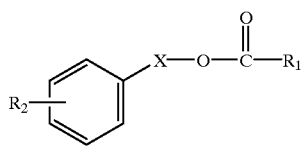

wherein
   $R_1$ is a $C_{17}$ to $C_{21}$ unsaturated hydrocarbon group which is linear or branched and is unsubstituted or substituted with a pendant hydroxyl group;
   X is $CH_2$, $OCH_2CH_2$ or $HC=CHCH_2$;
   and $R_2$ is H, $OCH_3$, $CH_3$ or $CH_2CH_3$.

6. The method according to claim 5 wherein $R_1$ contains at least two unsaturated carbon-carbon bonds.

7. The method according to claim 5 wherein X is $CH_2$ and $R_2$ is H.

8. The method according to claim 5 wherein $R_1$ contains at least one pendant hydroxyl group, X is $CH_2$ and $R_2$ is H.

9. A method of providing dry emolliency and high skin protection factor in a skin-protective or sunscreen composition comprising a pigment selected from $TiO_2$ and ZnO or a UV light absorbing compound selected from the group consisting of para-amino benzoic acid (PABA), octyl salicylate, octyl methoxycinnamate, p-dimethylamino benzoic acid ester of 2-ethylhexanol, avobenzone and mixtures, thereof, and additional components selected from the group consisting of water, solvents, emulsifiers, oils, suspending or dispersing agents, conditioning agents, UV absorbing compounds, additional pigments, fragrances and preservatives, said method comprising including in said composition an amount of an emollient ester comprising about 0.25% to about 20% by weight of said composition, said emollient ester having the structure:

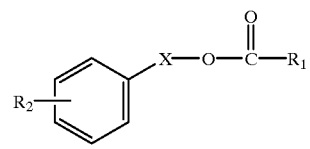

wherein
   $R_1$ is a $C_{17}$ to $C_{21}$ unsaturated hydrocarbon group which is linear or branched and is unsubstituted or substituted with a pendant hydroxyl group;
   X is $CH_2$, $OCH_2CH_2$ or $HC=CHCH_2$;
   and $R_2$ is H, $OCH_3$, $CH_3$ or $CH_2CH_3$.

10. The method according to claim 9 wherein $R_1$ contains at least two unsaturated carbon-carbon bonds.

11. The method according to claim 9 wherein X is $CH_2$ and $R_2$ is H.

12. The method according to claim 9 wherein $R_1$ contains at least one pendant hydroxyl group, X is $CH_2$ and $R_2$ is H.

13. A method of enhancing dry emolliency and gloss in a shampoo, conditioner, lipstick or lip balm composition comprising components selected from the group consisting of water, solvents, surfactants, emulsifiers, thickeners, coloring agents, preservatives, conditioning agents, humectants, waxes, oils, pigments, preservatives and flavoring agents, said method comprising including in said composition an effective amount of a compound according to the structure:

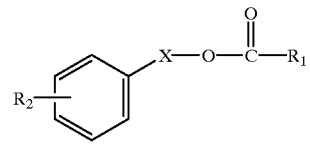

wherein
   $R_1$ is a $C_{17}$ to $C_{21}$ unsaturated hydrocarbon group which is linear or branched and is unsubstituted or substituted with a pendant hydroxyl group;
   X is $CH_2$, $OCH_2CH_2$ or $HC=CHCH_2$;
   and $R_2$ is H, $OCH_3$, $CH_3$ or $CH_2CH_3$.

14. The method according to claim 13 wherein $R_1$ contains at least two unsaturated carbon-carbon bonds.

15. The method according to claim 13 wherein X is $CH_2$ and $R_2$ is H.

16. The method according to claim 13 wherein $R_1$ contains at least one pendant hydroxyl group, X is $CH_2$ and $R_2$ is H.

17. An emollient compound for use in cosmetic, toiletry and personal care compositions according to the structure:

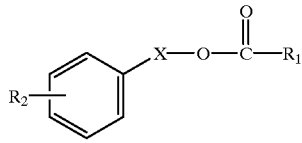

wherein $R_1$ is a $C_{17}$ to $C_{21}$ unsaturated hydrocarbon group which is linear or branched and is unsubstituted or substituted with a pendant hydroxyl group;

X is $CH_2$, $OCH_2CH_2$ or $HC=CHCH_2$;

and $R_2$ is H, $OCH_3$, $CH_3$ or $CH_2CH_3$.

18. The compound according to claim 17 wherein $R_1$ contains at least two unsaturated carbon-carbon bonds.

19. The compound according to claim 17 wherein X is $CH_2$ and $R_2$ is H.

20. The compound according to claim 17 wherein $R_1$ contains at least one pendant hydroxyl group, X is $CH_2$ and $R_2$ is H.

21. A cosmetic, toiletry or personal care composition consisting essentially of an emollient compound exhibiting the characteristics of dry emolliency according to the structure:

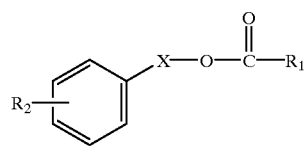

wherein $R_1$ is a $C_{17}$ to $C_{21}$ unsaturated hydrocarbon group which is linear or branched and is unsubstituted or substituted with a pendant hydroxyl group;

X is $CH_2$, $OCH_2CH_2$ or $HC=CHCH_2$;

and $R_2$ is H, $OCH_3$, $CH_3$ or $CH_2CH_3$, said compound being included in said composition in an effective amount within the range of about 0.05% to about 25% by weight of said composition, said composition further comprising at least one additional component selected from the group consisting of water, solvents, conditioning agents, surfactants, emulsifiers, thickeners, waxes, coloring agents, preservatives, humectants, medicaments, fragrances, oils, suspending agents, UV absorbers, flavorings, coloring agents and pigments.

22. The composition according to claim 17 wherein $R_1$ contains at least two unsaturated carbon-carbon bonds.

23. The composition according to claim 17 wherein X is $CH_2$ and $R_2$ is H.

24. The composition according to claim 17 wherein $R_1$ contains at least one pendant hydroxyl group, X is $CH_2$ and $R_2$ is H.

* * * * *